US011280775B2

(12) United States Patent
Hargrove et al.

(10) Patent No.: US 11,280,775 B2
(45) Date of Patent: Mar. 22, 2022

(54) SIMULTANEOUS GATED INTEGRATED DETECTION DEVICE AND PROCESS

(71) Applicants: James McChesney Hargrove, Highland Park, IL (US); John Hargrove, Costa Mesa, CA (US)

(72) Inventors: James McChesney Hargrove, Highland Park, IL (US); John Hargrove, Costa Mesa, CA (US)

(73) Assignee: ALTI, LLC, Highland Park, IL (US)

( * ) Notice: Subject to any disclaimer, the term of this patent is extended or adjusted under 35 U.S.C. 154(b) by 0 days.

(21) Appl. No.: 17/115,619

(22) Filed: Dec. 8, 2020

(65) Prior Publication Data

US 2021/0172920 A1 Jun. 10, 2021

Related U.S. Application Data

(60) Provisional application No. 62/945,207, filed on Dec. 8, 2019.

(51) Int. Cl.
*G01N 33/00* (2006.01)
*G01N 21/33* (2006.01)
*G01N 21/3504* (2014.01)
*G01J 3/42* (2006.01)

(52) U.S. Cl.
CPC ............ *G01N 33/0037* (2013.01); *G01J 3/42* (2013.01); *G01N 21/33* (2013.01); *G01N 21/3504* (2013.01); *G01N 2201/06113* (2013.01)

(58) Field of Classification Search
CPC ............... G01N 33/0037; G01N 21/33; G01N 21/3504; G01N 2201/06113; G01J 3/42
See application file for complete search history.

(56) References Cited

U.S. PATENT DOCUMENTS

2009/0273785 A1* 11/2009 Gundersen ......... G01N 33/0037
356/437

FOREIGN PATENT DOCUMENTS

WO 2000057156 A1 9/2000

OTHER PUBLICATIONS

PCT/US2020/063840. International Search Report & Written Opinion (dated May 14, 2021).

* cited by examiner

*Primary Examiner* — Jamil Ahmed
(74) *Attorney, Agent, or Firm* — Loza & Loza, LLP; Heidi Eisenhut; Mark L. Cooper

(57) ABSTRACT

A cavity ring down measurement system comprising a light source in optical communication with a detector through an optical cavity wherein the detector is in electronic communication through a gating circuit with a first integrating circuit and a second integrating circuit, controlled to obtain a ring up signal simultaneous with a ring down signal of a plurality of ON-OFF cycles over a single period of time. A process to utilize the system is also disclosed.

20 Claims, 5 Drawing Sheets

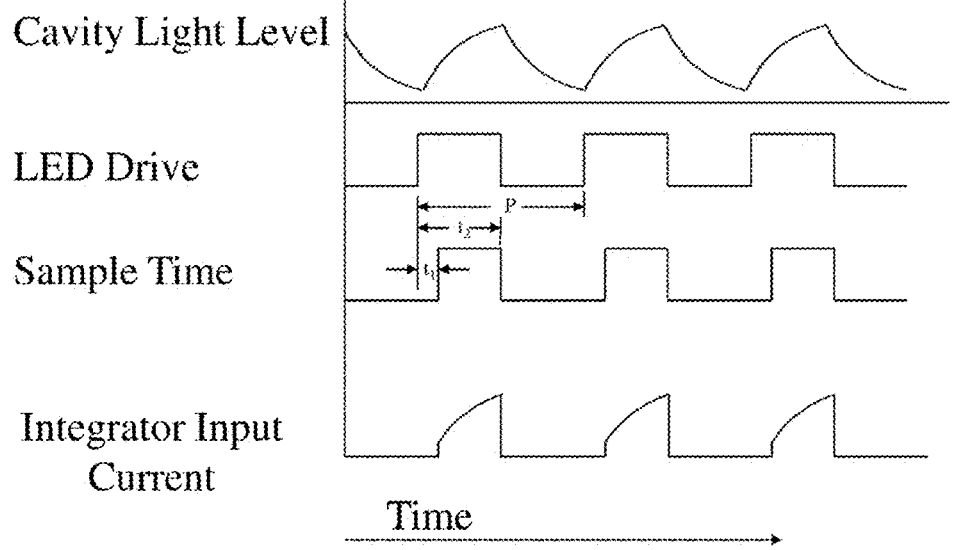
Rise Time Signal Measurement
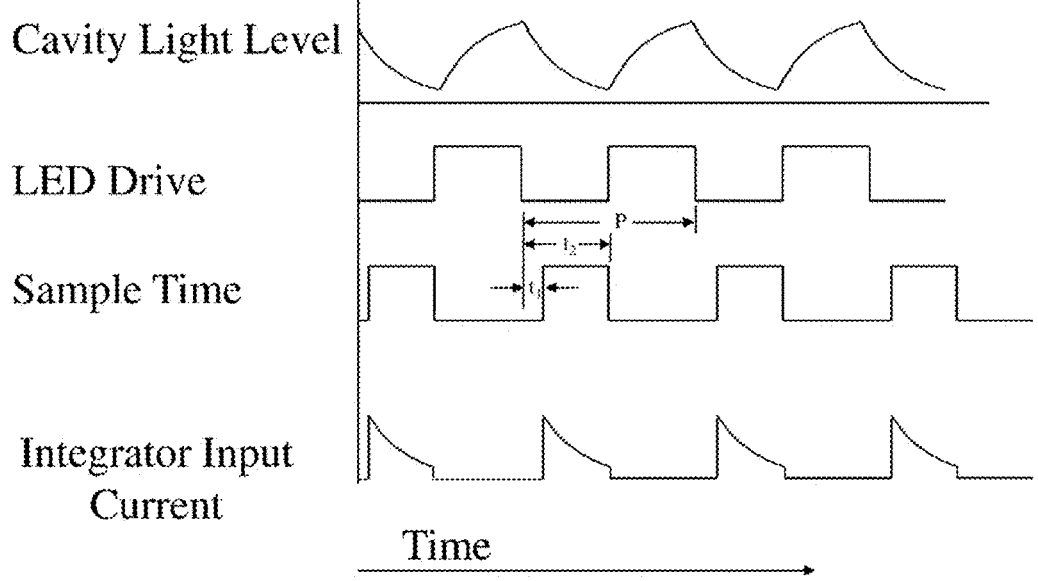
Fall Time Signal Measurement

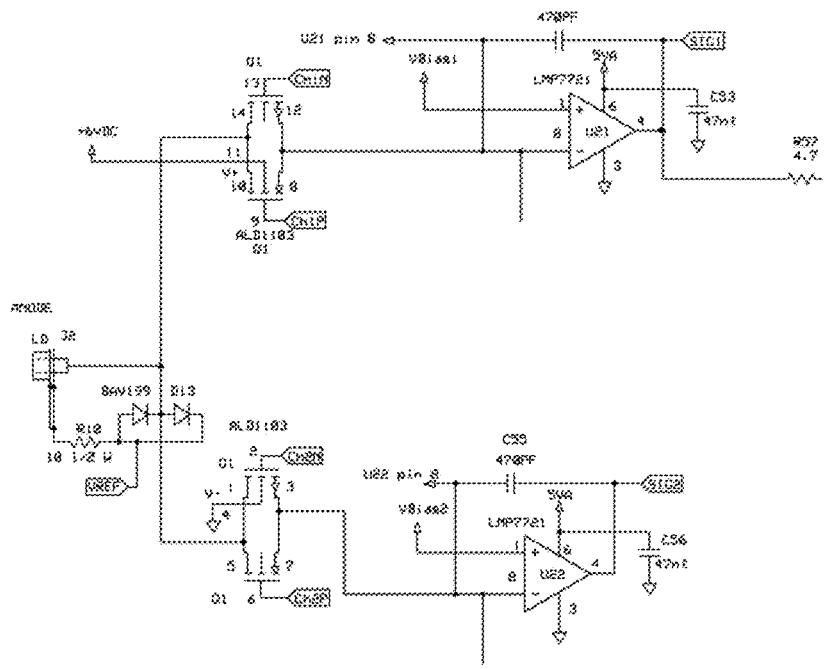
FIG. 6
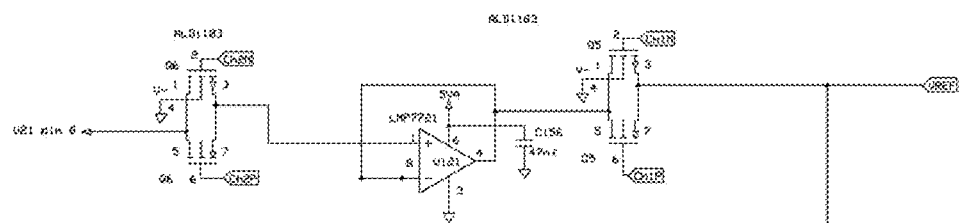
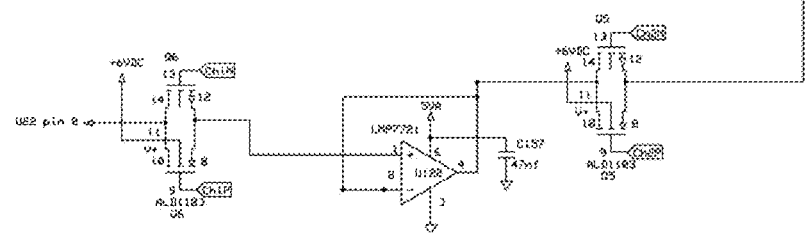
FIG. 7

SIMULTANEOUS GATED INTEGRATED DETECTION DEVICE AND PROCESS

CROSS REFERENCE TO RELATED APPLICATIONS

This application claims the benefit of and priority to provisional patent application U.S. 62/945,207, filed Dec. 8, 2019, the contents of which are fully incorporated by reference herein.

BACKGROUND

The instant disclosure generally relates to a system for cavity enhanced spectroscopy and a method of utilizing cavity enhanced spectroscopy. In particular, a system directed to detection and measurement of trace chemical species or particles in gaseous samples.

Air is a mixture of gases approximately composed of 78.08% nitrogen ($N_2$), 20.95% oxygen ($O_2$), 0.93% argon (Ar), 0.038% carbon dioxide ($CO_2$), trace amounts of other gases, and a variable amount (average around 1%) of water vapor. At ambient temperatures, the oxygen and nitrogen gases in air will not react with each other. However, in an internal combustion engine, combustion of a mixture of air and fuel produces combustion temperatures high enough to drive endothermic reactions between atmospheric nitrogen and oxygen in the flame, yielding various oxides of nitrogen, such as nitric oxide (NO) and nitrogen dioxide ($NO_2$). Mono-nitrogen oxides such as NO and $NO_2$ are typically referred to by the generic term $NO_N$. In addition, some materials may be made to produce nitrogen dioxide, and/or other volatile analytes. Measurement of these volatile analytes in the ambient air proximate to their location may be used as an indicator of the presence of these materials.

Although techniques have been developed to measure $NO_2$, and other volatile analytes, these techniques have deficiencies related to interferences, stability and precision. As a result, the measurement of $NO_2$ and other volatile analytes may not be accurate. A more stable instrument and precise methods of measurement of these compounds is needed.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect of the disclosure, a process comprises the steps of providing a cavity ring down instrument comprising a light source in optical communication with a detector through an optical cavity; the detector in electronic communication with a first integrating circuit and a second integrating circuit; over an integrating period of time, repeatedly cycling the light source on in a light-source-on event to produce a plurality of individual ring up currents from the detector, each of the individual light-source-on events followed by a corresponding light-source-off event to produce a plurality of ring down currents from the detector; for each of the light-source-on events and each of the light-source-off events, over the integration period of time, directing a portion of each ring up current to the first integrating circuit followed by directing a portion of each ring down current to the second integrating circuit to produce a total ring up current comprising a sum of the plurality of ring up currents obtained during the integration time and a total ring down current comprising a sum of the plurality of ring down currents obtained during that same integration time; determining a rise time from the total ring up current; and determining a fall time from the total ring down current.

In another aspect of the disclosure, a system comprises a light source in optical communication with a detector through an optical cavity; the detector in electronic communication through a gating circuit with a first integrating circuit and a second integrating circuit; the light source, the detector, the gating circuit, and the integrating circuits in electronic communication with a processing system; the processing system configured, over an integrating period of time, to repeatedly cycle the light source on in a light-source-on event to produce a plurality of individual ring up currents from the detector, each of the individual light-source-on events followed by a corresponding light-source-off event to produce a plurality of ring down currents from the detector; for each of the light-source-on events, over the integration period of time, a portion of each ring up current is directed by the gating circuit to the first integrating circuit to produce a total ring up current including a sum of the plurality of ring up currents obtained during the integration time; for each of the light-source-off events, over the integration period of time, a portion of each ring down current is directed by the gating circuit to the second integrating circuit to produce a total ring down current including a sum of the plurality of ring down currents obtained during that same integration time.

BRIEF DESCRIPTION OF THE DRAWINGS

FIG. 2 is a graphical representation of a "rise" time signal measurement generated during a predetermined time period according to one or more aspects of the disclosure;

FIG. 3 is a graphical representation of a "fall" time signal measurement generated during a predetermined time period according to one or more aspects of the disclosure;

FIG. 6 is a schematic representation showing the switching or gating circuitry for an integration circuit according to one or more aspects of the disclosure; and FIG. 7 is a schematic representation showing the end of cycle sampling circuitry according to one or more aspects of the disclosure.

DETAILED DESCRIPTION

Figure 1:
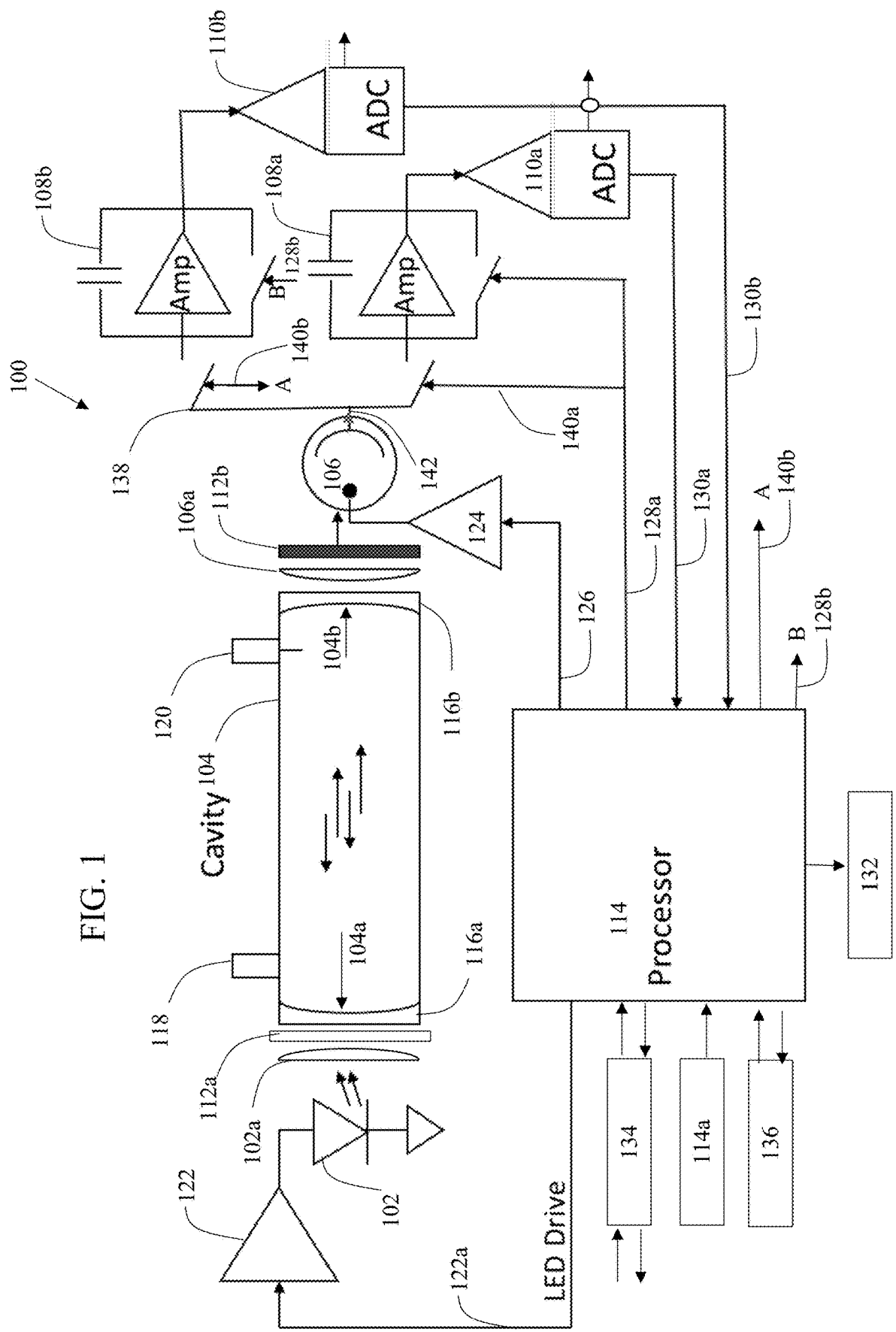
FIG. 1 illustrates a schematic of a cavity ring down system according to one or more aspects of the disclosure.

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context.

Also, in the summary and this detailed description, it should be understood that a physical range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

It is to be understood that various embodiments of the present disclosure will be described with reference to the accompanying drawings. Accordingly, those of ordinary skill in the art will recognize that modifications, equivalents, and/or alternatives of the various embodiments described herein can be made without departing from the scope and spirit of the present disclosure. With regard to description of drawings, similar components may be marked by similar reference numerals.

For use herein, the expressions "have", "may have", "include", "comprise", "may include", and "may comprise" indicate the existence of corresponding features (e.g., such as numeric values, functions, operations, or components) but do not exclude the presence of additional features.

In the present disclosure, expressions such as, "A or B", "at least one of A or/and B", and "one or more of A or/and B", may include any and all combinations of one or more of the associated listed items. For example, the terms "A or B", and "at least one of A or B" may refer to the case (1) where A is included, (2) where B is included, or (3) where both A and B are included.

Terms such as "first", "second", and the like used herein may refer to various elements of various embodiments of the present disclosure, but do not limit the elements. For example, such terms are used only to distinguish an element from another element and do not limit the order and/or priority of the elements. For example, a first user device and a second user device may represent different user devices irrespective of sequence or importance. For example, without departing from the scope of the present disclosure, a first element may be referred to as a second element, and similarly, a second element may be referred to as a first element.

It will be understood that when an element (for example, a first element) is referred to as being operatively or communicatively "coupled with/to" or "connected to" another element (for example, a second element), it can be directly coupled with/to or connected to the other element or an intervening element (for example, a third element) may be present.

As used herein, the expression "configured to" used herein may be used interchangeably with, for example, the expression "suitable for", "having the capacity to", "designed to", "adapted to", "made to", or "capable of". The term "configured to (or set to)" does not mean only "specifically designed to" in hardware. Instead, the expression "a device configured to" may mean that the device is "capable of" operating together with another device or other components. For example, an "electronic memory assembly" configured to (or set to) store data for subsequent retrieval, refers to any such memory module or modules, with the associated circuitry, power source, and programming which render it capable of performing the corresponding operation of storage and retrieval utilizing a generic-purpose processor (e.g., a central processing unit (CPU) or an application processor) which may perform corresponding operations by executing one or more software programs which are stored on the memory device.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, EPROM memory, EEPROM memory, registers, a hard disk, a removable disk, a CD-ROM and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The controller and/or processor refers to a controlling system which typically includes a processor and the related circuitry and components, e.g., power source, memory, storage, processors, coprocessors, gates, relays, other integrated circuits, software, and/or the like, necessary for its function. The processor may be responsible for managing general processing, including the execution of software stored on a machine-readable media. The processor may be implemented with one or more general-purpose and/or special-purpose processors. Examples include microprocessors, microcontrollers, DSP processors, and other circuitry that can execute software. Software shall be construed broadly to mean instructions, data, or any combination thereof, whether referred to as software, firmware, middleware, microcode, hardware description language, or otherwise. Machine-readable media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may comprise a computer-readable medium having instructions stored (and/or encoded) thereon, the instructions being executable by one or more processors to perform the operations described herein and be embodied in a computer-program product. The computer-program product may comprise packaging materials to advertise the computer-readable medium therein for purchase by consumers.

Computer readable medium may also include, by way of example, a carrier wave, a transmission line, and any other suitable medium for transmitting software and/or instructions that may be accessed and read by a computer or the processor. The non-transient computer readable medium may reside in the device, external to the device, or distributed across multiple entities including the device. The non-transient computer readable medium may be embodied in a computer program product. By way of example, a computer program product may include a computer readable medium in packaging materials. Those skilled in the art will recognize how best to implement the described functionality presented throughout this disclosure depending on the particular application and the overall design constraints imposed on the overall system.

Within the present disclosure, the word "exemplary" and/or "preferably" are used to mean "serving as an example, instance, or illustration." Any implementation or aspect described herein as "exemplary" and/or "preferably" are is not necessarily to be construed as preferred or advantageous over other aspects of the disclosure in an overall limiting sense, but only in relation to specific embodiments. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other. For instance, a first object may be coupled to a second object even though the first object is never directly physically in contact with the second object. The terms "circuit" and "circuitry" are used broadly, and intended to include both hardware implementations of electrical devices and conductors that, when connected and configured, enable the performance of the functions described in the present disclosure, without limitation as to the type of electronic circuits, as well as software implementations of information and instructions that, when executed by a processor, enable the performance of the functions described in the present disclosure.

One or more of the components, steps, features and/or functions illustrated in the figures may be rearranged and/or combined into a single component, step, feature or function or embodied in several components, steps, or functions. Additional elements, components, steps, and/or functions may also be added without departing from novel features disclosed herein. The apparatus, devices, and/or components illustrated in the figures may be configured to perform one or more of the methods, features, or steps described herein. The novel algorithms described herein may also be efficiently implemented in software and/or embedded in hardware.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order and are not meant to be limited to the specific order or hierarchy presented unless specifically recited therein.

The terms used herein are used to describe specific embodiments of the present disclosure and are not intended to limit the scope of the present disclosure. The terms of a singular form may include plural forms unless otherwise specified. Unless otherwise defined herein, all the terms used herein, which include technical or scientific terms, may have the same meaning as that generally understood by a person skilled in the art to which the present disclosure pertains. It will be further understood that terms, which are defined in a dictionary and commonly used, should also be interpreted as is customary in the relevant related art and not in an idealized or overly formal manner unless expressly so defined herein. In some cases, even if terms are defined in the specification, they may not be interpreted to exclude embodiments of the present disclosure.

In various embodiments of the present disclosure, the electronic components referred to in embodiments of the device is not limited to currently known devices but may include new electronic devices suitable for the intended purpose which are subsequently produced due to the development of new technologies.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Furthermore, "determining" may include resolving, selecting, choosing, establishing and the like. Likewise, "controlling" encompasses a wide variety of actions, the totality of which results in the functioning of the device for the intended purpose.

The following detailed description is of the best currently contemplated modes of carrying out the various aspects of the disclosure. The description is not to be taken in a limiting sense, but is made merely for the purpose of illustrating the general principles of the aspects of the disclosure.

Applicant has discovered that the measurement of nitrogen dioxide ($NO_2$) in ambient air within an environment may be useful to determine the presence and amount of various materials including explosives, narcotics, and the like present within this environment. Analysis may include conversion of analytes to $NO_2$ and/or conversion of $NO_2$ to nitric oxide (NO), either by catalytic thermal decomposition (which suffers from interferences from organic nitrates, HONO, $HNO_3$, and the like) and/or by photolysis (which is relatively immune from interferences), when followed by reaction of NO with $O_3$ to produce electronically excited $NO_2^*$. The excited $NO_2^*$ emits a broad continuum radiation in the region of 500-900 nanometers (nm), with a signal strength that is proportional to the concentration of NO. Subtraction of the background NO concentration then yields the concentration of $NO_2$ in the sample, which may then be utilized to determine a concentration of a particular material or class of materials present in this space.

Chemiluminescence of nitric oxide (NO) by reaction with ozone is used extensively for quantifying NO and nitrogen dioxide ($NO_2$) in industrial smokestack emissions, air quality monitoring stations and medical facilities, but suffers from quenching by water vapor and, at high enough concentrations, from $CO_2$, as well leading to erroneously low readings. An additional problem for $NO_2$ measurements using chemiluminescence is that catalytic thermal decomposition of $NO_2$ to NO for detection together as $NO_N$, where x=1 and/or 2, can lead to high $NO_2$ readings from other nitrogen-containing species, such as acyl peroxynitrates (PANs), alkyl nitrates and ammonia which all produce $NO_2$ upon thermal decomposition. This additional signal has resulted in $NO_N$-analyzers being termed $NO_N$-analyzers because they measure more than the sum of NO and $NO_2$. In the presence of quenching, the analyzers can actually indicate significantly less pollution as well. As a result, accurate measurements of $NO_2$ using the prior art approach of chemiluminescence cannot be reliably obtained.

In embodiments of the instant disclosure, $NO_2$ specific analyzers with low limits of detection are disclosed which utilize an improved cavity ring-down spectroscopy (CRDS) and its derivatives, continuous wave cavity ring-down spectroscopy (cw-CRDS), off-axis cw-CRDS, cavity attenuated phase shift spectroscopy (CAPS), and cavity enhanced absorption spectroscopy (CEAS). Tunable diode laser spectroscopy (TDLAS) and laser induced fluorescence (LIF) are more established techniques that measure $NO_2$ and could also be combined with chemiluminescence.

CRDS is a sensitive spectroscopic technique that is based on measurements of the rate of attenuation (k) rather than the magnitude of attenuation of the light by a sample. It can be used to measure the concentration of some light-absorbing substances, such as air pollutants. In CRDS, two ultra-high reflective mirrors face each other with a space (or cavity) in between. In the conventional pulsed laser implementation, a brief pulse of light is injected into the cavity and bounces (i.e., "rings") back and forth between the mirrors. Some small amount (typically around 0.1% or less) of the generated light enters and leaks out of the cavity and may be measured each time light hits one of the mirrors. As some light is lost (i.e., leaks out) on each reflection, the amount of light hitting the mirrors is slightly less each time. Furthermore, as a percentage leaks through, the amount of light measured also decreases with each reflection. If the only loss factor in the cavity is the reflectivity loss of the mirrors, one can show that the light intensity inside the cavity decays exponentially in time with a decay constant tau ($\tau$) (i.e., the "ring down time"). If a light-absorbing species is introduced into the cavity, the light will undergo fewer reflections before it disappears. In other words, CRDS measures the time it takes for the light to drop to a certain percentage of its original amount. The time change measured may be converted to a concentration.

As the absorption described above involves hundreds to thousands of passes of light through the sample, the sensitivity is greatly enhanced. CRDS is capable of measuring species of known absorption cross sections by taking the difference between the ring-down decay rate with sample ($1/\tau$) and the background decay rate without sample ($1/\tau_0$) and multiplying by $L/cl_s$:

$$\alpha = \frac{L}{cl_s}\left(\frac{1}{\tau} - \frac{1}{\tau_0}\right) = \sigma N \qquad \text{Equation 1}$$

where $\alpha$ is the absorption coefficient, c is speed of light, L is the cavity length, and $l_s$ is the sample path length. The resulting absorption coefficient, $\alpha$, can then be divided by the known cross section of the sample, or sigma ($\sigma$), to yield the concentration or number density (N).

In some prior art arrangements, phase shift measurements have relied on the use of quadrature lock-in amplifiers which are not sufficiently accurate at the modulation frequencies encountered in this type of device to provide high phase resolution. In other prior art arrangements, a frequency divider chain starting from a single clock and generating both in-phase and quadrature reference signals is used.

Additionally, prior art pertaining to detection of signal time decay relies on high-speed sampling of the decaying signal followed by conversion to a digital signal. This technique requires the use of an expensive combination of a laser, a photomultiplier, high-speed sampling and digitizing circuitry. In other prior art pertaining to detection of signal time decay, each modulation cycle of the light source is divided into a finite number of equal consecutive windows followed by integration of the light signal recorded during each of those windows. These windows may be generated by division from a single frequency source. Both methods suffer from deficiencies with respect to precision, cost and robustness of the method.

According to one or more aspects of the disclosure, a cavity ring down system can be optimized to precisely measure trace gases in an air sample by using time sampling detection and multiple-sample averaging resulting in a high signal-to-noise ratio. In one embodiment, a cavity ring down system is programmed to measure the rise time and the fall time of the light level in an optical cavity. These values are combined to form a ratio (see Equation 2) that can be used to find the decay time constant (see Equation 3).

More specifically, the cavity ring down system is programmed to integrate a plurality of sample portions during a rise time and a plurality of sample portions during a fall time (in alternate intervals). In one implementation, a series of rise time data and a series of fall time data are collected in alternate intervals. Each integrated series gives an indication of the characteristic time constant ($\tau_0$) of the cavity that is used to generate a reference time constant (see Equation 1). When the rise time measurement and fall time measurement (or successive pairs of measurements) are added (i.e., rise time plus fall time), the sum represents the full-scale signal and provides an indication of the intensity of the light source that is needed to most accurately calculate the time constant ($\tau_0$) (see Equation 1). Additionally, the absolute difference (i.e., rise time minus fall time) between the rise time measurement and the fall time measurement can also be calculated and divided by the sum (full-scale signal). When the ratio, i.e., (the rise time minus the fall time) is divided by (the rise time plus the fall time), represented by the formula:

$$\text{Ratio} = \frac{\text{rise time} - \text{fall time}}{\text{rise time} + \text{fall time}} \qquad \text{Equation 2}$$

This Ratio along with the period (P), the start time of sampling ($t_1$) and the end time of sampling ($t_2$) can be input into the following equation to reiteratively solve for the decay time constant ($\tau$):

$$\text{Ratio} = 1 + 2\left(1 - \frac{e^{\left(\frac{-P}{2\tau}\right)}}{1 + e^{\left(\frac{-P}{2\tau}\right)}}\right)\left(\frac{\tau}{(t_2 - t_1)}\right)\left(e^{\left(\frac{-t_2}{\tau}\right)} - e^{\left(\frac{-t_1}{\tau}\right)}\right). \qquad \text{Equation 3}$$

The decay time constant (τ) is assumed to be the same for the rise time. The decay time constant (τ) is used to calculate the decay rate (k) as the inverse of the decay time constant (τ) by the following equations:

$$\text{Rate} = k = \frac{1}{\tau}, \quad \text{Equation 4}$$

and $$\alpha = \frac{1}{c}(k - k_0), \quad \text{Equation 5}$$

where c is the speed of light, k is the rate obtained in Equation 3 (with sample) and $k_0$ is the rate obtained when the cell is empty (no sample). The absorption coefficient can then be used to calculate the number density (N) by the following formula:

$$N = \frac{\alpha}{\sigma}, \quad \text{Equation 6}$$

where N is the number density and σ is the cross section of the absorbing or scattering species. The concentration in parts per million or parts per billion may be obtained by dividing the number density by the total number density ($N_T$) corrected for pressure (P) and temperature (T) where k is the Boltzmann constant.

$$N_T = \frac{P}{kT}, \quad \text{Equation 7}$$

and $$\text{Concentration }(ppb) = \frac{N}{N_T} \times 10^{-9}. \quad \text{Equation 8}$$

In an alternative embodiment, a cavity ring down system is programmed to measure the total signal intensity ($I_o$) and one of the rise time or fall time to obtain a rate equation which can be used to solve for the rate of the sample (or no sample) (see Equation 4; Equations 5-8). More particularly, $I_o$ may be obtained by taking a measurement while the light source is ON and taking a measurement while the light source is OFF The difference between these two measurements is $I_o$. These measurements are taken after the decay and rise of light in the light cavity occur whereas the rise and fall times are taken immediately after the light is turned on or off. Either the integrated decay rate or the integrated rise rate can then be divided by $I_o$ to obtain the rate equation which can subsequently be used to obtain a rate equation which can be used to solve for the rate of the sample (or no sample). Either the decay rate or the rise rate can be calculated independently from the following equations:

$$\int_{t_1}^{t_2} S dt = I_o(e^{kt_2} - e^{kt_1}), \quad \text{Equation 9}$$

$$\int_{t_1}^{t_2} S dt = I_o(t_2 - t_1 - e^{-kt_2} + e^{-kt_1}). \quad \text{Equation 10}$$

The CRDS systems which utilize gated integrated detection has been shown effective. However, such systems are prone to drift and can always benefit from reduced limits of detection. Gated Integrated Detection has been used to sample 100 microseconds (ms) of Rise and 100 ms of Fall in sequence for a 250 ms sample period.

One or more aspects of the disclosure are directed to Applicant's discovery that a significant advantage may be obtained in detection limit and precision when a plurality of both the rise current (light-source-ON event) and fall current (light-source-OFF event) of the SGID are acquired simultaneously during the same analysis time instead of being acquired in a serial or sequential manner over different integration time periods, i.e., determining one followed by determining the other. In embodiments, over the same analysis period, the electronic signal of a plurality of both rise and fall events are measured concurrently, switched in parallel to and summed by separate integrators, instead of acquiring each of the gated events in a series, e.g., summing a plurality of rise currents followed by summing a plurality of fall currents of the system. The result is a baseline-drift free analyzer with a factor of at least 2 increase in duty cycle.

In addition, embodiments disclosed herein are able to utilize a rugged detector such as a photodiode which is suitable to be switched according to embodiments disclosed herein to achieve an improvement of as much as a factor of 3 increase in sensitivity over a phototube or other similar detectors.

Applicant has further discovered that embodiments disclosed herein work well with $NO_2$ at about 405 nm. However, it is to be understood that the instant disclosure is not limited in this way and will also provide improved benefits utilizing UV, visible, NIR and/or IR regions of the spectrum. Accordingly, embodiments disclosed herein may also be suitable for detection of other species such as ammonia, methane, nitrogen monoxide, nitrous oxide, nitrogen trioxide, carbon monoxide, carbon dioxide, ethylene oxide, phosgene, ozone, oxygen, sulfur dioxide, and/or the like.

One such example includes systems in which some species are converted into others prior to analysis, such as, for example, the conversion of fentanyl to nitrogen dioxide when titrated with ozone at 100-300° C. prior to analysis utilizing a cavity ring down measurement system according to one or more embodiments disclosed herein.

In embodiments, a cavity ring down measurement system comprises a light source in optical communication with a detector through an optical cavity; the detector in electronic communication with a first integrating circuit and a second integrating circuit; the light source, the detector, the gating means, and the integrating circuits in electronic communication with an electronic control system, such that the system is controlled to, over an integrating period of time, repeatedly cycle the light source on in a light source on event to produce a plurality of individual ring up currents from the detector, each of the individual light source on events followed by a corresponding light source off event to produce a plurality of ring down currents from the detector; for each of the light source on and off events, over the integration period of time, a portion of each ring up current is individually directed, typically by associated gating circuitry, to the first integrating circuit followed by individually directing a portion of each ring down current to the second integrating circuit to produce a total ring up current comprising a sum of the plurality of ring up currents obtained during the integration time and a total ring down current comprising a sum of the plurality of ring down currents obtained during that same integration time.

In embodiments, the detector is in gated electronic communication with the first integrating circuit and with the second integrating circuit through at least one field effect transistor. In one or more embodiments, the light source is light-emitting diode or a laser. In related embodiments, the light source is a multimode laser, preferably a multimode laser having a bandwidth of at least 10 nm which may also be coupled to a 10 nm band pass filter. In one or more embodiments, the detector is a photo-diode, a phototube, and/or the like, along with the associated circuitry, preferably a photo-diode.

In one or more embodiments, the optical cavity has an effective optical length of greater than or equal to about 10 m, preferably greater than or equal to about 50 m, preferably greater than or equal to about 100 m, and less than or equal to about 10,000 m, preferably less than or equal to about 5,000 m, preferably less than or equal to about 1,000 m.

In embodiments, at least the light source, the detector, and the plurality of integrator circuits are in electronic communication and electronically controlled by an electronic control system, typically comprising one or more processors, memory, software, storage, and power source required to operate the device and collect, process, store and communicate the data.

In one or more embodiments, a process comprises the steps of providing a cavity ring down instrument comprising a light source in optical communication with a detector through an optical cavity according to one or more embodiments disclosed herein. In embodiments, the detector in electronic communication with a first integrating circuit and a second integrating circuit, preferably gated communication (e.g., switched), preferably through one or more field effect transistors. Over an integrating period of time of the process, the process further comprises repeatedly cycling the light source on in a light source on event to produce a plurality of individual ring up currents from the detector, each of the individual light source on events followed by a corresponding light source off event to produce a plurality of ring down currents from the detector. For each of the light source on and off events, over the integration period of time, at least a portion of each ring up current is directed to the first integrating circuit followed by directing at least a portion of each ring down current to the second integrating circuit. The plurality of ring up currents are integrated over the integration time to produce a total ring up current comprising a sum of the plurality of ring up currents obtained during the integration time simultaneous with the plurality of ring down currents being integrated over the integration time to produce a total ring down current comprising a sum of the plurality of ring down currents obtained during that same integration time. From these total ring up and total ring down currents a rise time is determined from the total ring up current; and a corresponding fall time is determined from the total ring down current.

In embodiments, the first integrating circuit comprises a first dual N-channel and dual P-channel MOSFET pair connected to the detector, e.g., configured for receiving a first detection signal; a first operational amplifier having a positive input for receiving a first dual N-channel and dual P-channel MOSFET pair output signal and a negative input for receiving a first operational output signal, and a second dual N-channel and dual P-channel MOSFET pair electrically connected to, e.g., configured to receive, the first operational output signal. Likewise, in embodiments, the second integrating circuit comprises: a third dual N-channel and dual P-channel MOSFET pair connected to the detector for receiving, e.g., configured to receive, a second detection signal from the detector; a second operational amplifier having a positive input for receiving a third dual N-channel and dual P-channel MOSFET pair output signal and a negative input for receiving a second operational output signal; and a fourth dual N-channel and dual P-channel MOSFET pair is configured to receive the second operational output signal.

In one or more embodiments of the process, a time for a single light source on and/or a single light source off event is less than or equal to about 500 microseconds (μs), preferably less than or equal to about 200 μS, preferably less than or equal to about 100 μs and greater than or equal to about 0.5 μs, preferably greater than or equal to about 1 μs, preferably greater than or equal to about 10 μs.

In one or more embodiments of the process, the integrating period of time is greater than or equal to about 0.01 seconds (s), preferably greater than or equal to about 0.1 s, preferably greater than or equal to about 0.5 s, and less than or equal to about 10 s, preferably less than or equal to about 5 s, preferably less than or equal to about 1 s.

In one or more embodiments of the process, cycling of the light source e.g., a laser, an LED, and/or the like, between an ON state or event (illuminated) and an OFF state or event (not illuminated) is controlled by a square wave electronic signal. The light produced by a light ON event enters a cavity through a first of the two nearly confocal dielectric mirrors that reflect the light thousands of times. During this process, light is lost through both of the confocal dielectric mirrors. The light lost through the second confocal mirror proximate to the detector is concentrated onto the detector. Eventually, the intensity of the light is below the detection capability of the detector. Accordingly, an optical cavity having a physical dimension of 10 cm between the two mirrors may have an effective optical length from about 10 m to greater than 10,000 meters. Accordingly, at least a portion of the light that escapes from the optical cavity is then directed to a detector, which converts the photons into electrons, e.g., an electronic signal, also referred to herein as a detector current proportional to the intensity of the light.

A portion of each electronic signal produced by the detector (the electrons) are switched between two channels, each channel in gated or switched electrical communication with an integration circuit. this switching or gating is timed to isolate both rise or ring up event currents (signals) which are directed to a first of the integration circuits and fall or ring down event currents (signals) which are directed to the second of the integration circuits.

This arrangement allows the two channels to integrate a plurality of the separate signals over an integrating period of time, e.g., on a capacitor associated with a particular integration circuit, thus a plurality of signals are summed to collect a higher signal than is produced by a single ON-OFF event. In embodiments, the integrating period of time is selected such that a total ring up current and/or a total ring down current is greater than or equal to about 100 mV, preferably greater than or equal to about 500 mV, preferably greater than or equal to about 1 volt of signal, which can be measured easily and accurately.

The rise and fall voltages, also referred to herein as the total ring up currents (or voltage) and total ring down currents (or voltage), are converted to a ratio that can be converted to a time constant with the appropriate calculations. The reciprocal of the time constant is a rate.

The difference between a cavity rate when the optical cavity is filled with a sample and a cavity rated of the optical cavity filled with background or ambient air without an increased concentration of the analyte above ambient conditions (e.g., baseline) is used to quantitatively determine the absorbance by dividing by the speed of light.

The absorbance is converted to concentration dividing by the cross section of the analyte and then dividing by the number density of pure air at sample temperature and pressure. Number density is in units of molecules per $cm^3$, and cross section is $cm^2$ per molecule. Absorbance is typically $cm^{-1}$ The existence of a reliable signal is used to determine whether the analyte is present. Typically, 6 sigma of the noise level is sufficient to avoid false positives.

FIG. 1 is a block diagram illustrating the SGID-CRDS according to an embodiment of the disclosure. Principle components of SGID-CRDS 100 generally include a light source 102, an optical cavity 104, a detector 106, a first integrator 108a, a second integrator 108b and a converter 110. Light source 102 with the aid of an associated lens or lenses 102a may be directed toward a proximal end 104a of optical cavity 104 while a distal end 104b of optical cavity 104 may be directed toward detector 106 with the aid of an associated lens 106a. In one embodiment, a bandpass filter 112a is positioned between light source 102 and proximal end 104a of optical cavity 104, and/or a bandpass filter 112a is positioned between distal end 104b of optical cavity 104 and detector 106 and/or proximate to the detector 112b. Detector 106 is in gated electrical communication through the switching circuitry 138, e.g., one or more field effect transistors, with integrators 108a and 108b. The integrators 108a and 108b are in electrical communication with the respective converter 110a and 110b. All components (i.e., light source 102, optical cavity 104, detector 106, integrators 108a and 108b, and converters 110a and 110b) are in electronic communication with and controlled and/or driven by a processing or controlling component, generally referred to in the figure as processor/computer and/or a processor system 114. An oscillator 114a may be utilized to provide a stable and accurate timing source for processor 114 instruction stepping and timing and, in turn, for the gated integration measurement intervals according to embodiments of the disclosure.

In one embodiment, light source 102 may be a noncoherent light source such as a light-emitting diode (LED). Other examples of light sources include, but are not limited to, a laser, a blackbody radiator, a flashlamp discharge or other gas discharge. In embodiments in which light source 102 is an LED, the LED color and bandpass filter color are selected to provide light in a preferred narrow spectral bandwidth, for example, between about four-hundred and two (402) nanometers to about four-hundred and twelve (412) nanometers.

In one embodiment, optical cavity 104 may include two highly reflective plano/concave mirrors 116a and 116b situated internally at each end therein (i.e., at proximal end 104a and distal end 104b of optical cavity 104). Each mirror 116a, 116b may have a diameter of approximately one inch (2.54 centimeters). In some embodiments, optical cavity 104 may have a cylindrical shape and may be, for example, between about 0.25 inches (0.635 centimeters) to about 1.50 inches (3.81 centimeters) in diameter, preferably about one inch (2.54 centimeters) in diameter, i.e., approximately close to the effective diameter of each mirror 116a, 116b. The distance between mirrors 116a and 116b may be, for example, between about five (5) inches (12.7 centimeters) and about fifty (50) inches (127 centimeters). According to one embodiment, a sample inlet 118 is in fluid communication with (or coupled to) optical cavity 104, and, similarly, a pump inlet 120 is also in fluid communication with (or coupled to) optical cavity 104. During operation of CRDS 100, a sample may be introduced into optical cavity 104 via sample inlet 118 and removed from optical cavity 104 via pump inlet 120.

In one embodiment, detector 106 with the aid of lens 106a and/or filters 112b (i.e., proximate to distal end 104b of optical cavity 104) functions to collect photons emitting from optical cavity 104 continuously or during predetermined time intervals (explained in more detail below). Detector 104 may be, for example, a phototube (PT), a photomultiplier tube (PMT), or an avalanche photodiode (APD). Integrators 108a and 108b are in gated (switched) electrical communication with detector 106 through the gating circuitry generally represented as 138. Each integrator, in turn, collects a current sample from detector 106 while a corresponding converter 110a or 110b in electrical communication with the integrator 108a or 108b, respectively, measures output voltage from the corresponding integrator.

According to one method, computer 114 drives light source 102 (arrow 122a), e.g., LED 102, via an amplified buffer 122 by generating a square wave input current which results in LED 102 being repeatedly turned ON and OFF. The amplified buffer 122 may use a constant current source to stabilize the output light level of the LED 102. The period of the resultant modulated current is chosen to be approximately $1/(4*\tau)$ where $\tau$ is a time in microseconds. For example, if $\tau$ is two (2) microseconds, then the LED drive period would be eight (8) microseconds and the frequency would be nominally one-hundred and twenty-five (125) kilohertz (KHz). In another example, if $\tau$ is twenty (20) microseconds, then the LED drive period would be eighty (80) microseconds and the frequency would be nominally twelve and one-half (12.5) KHz. Pulsed light emanating from LED 102 then illuminates optical cavity 104. The light level in optical cavity 104 builds up, i.e., rises, while LED 102 is ON and then decays, i.e., falls, while LED 102 is OFF.

The light escaping from distal end 104b of optical cavity 104 is focused on to detector 106 with the aid of lens 106a which in turn converts the photons from the light into electrons. Detector 106 collects the photons emitted from optical cavity 104 only when gated (i.e., driven ON by an amplified buffer 124). During a single ON-OFF event, portions of two separate measurements made. During a portion of the ON event, the output from the detector is directed, e.g., gated or switched into electrical communication 138 with a first integration circuit 108a. During this time the current 142 flowing from the detector 106 is integrated by integrator 108a. Immediately after the ON event the light source 102 is switched off by processor 114 to produce an OFF event. During a portion of the OFF event, the output of the detector 106 is directed through the gating circuit 138 to the second integrator 108b. The current 142 flowing from the detector 106 is then integrated by integrator 108b. A plurality of ON-OFF events are conducted during a single integration period of time. The sum of each of the currents from each of the portions of an ON event obtained during the integration time are integrated to produce an electronic signal which represents a total ring up time. The sum of each of the currents from each of the portions of an OFF event obtained during this same integration time are integrated to produce an electronic signal which represents a total ring down time. The gating circuit 138 is controlled by the processor 114 via communication links 140a and 140b. The sample time signal output (arrow 126) from computer 114 to detector 106 defines this gated detection time (see FIGS. 2-3). Each ON event and OFF event produces a small current sample which is collected by integrators 108*a* and 108*b*. This process is repeated over, for example, ten-thousand to one hundred thousand times during a single integration period of time, (e.g., 10-100 µs ON-OFF cycle time over an integration period of time of about 0.1 to 1 second) which in turn creates a significant output voltage at integrators 108*a* and 108*b* (see FIG. 4). The output voltage is then measured by a corresponding converter 110*a* or 110*b*, each of which may be, for example, a high-resolution analog-to-digital converter. After the end of the previous measurement cycle (integration period of time) and before the beginning of the next measurement cycle, the integrators 108*a* and 108*b* and the corresponding circuitry may be reset (arrows 128*a* and 128*b*) by computer 114 and the initial output voltage of the integrators 108*a* and 108*b* may be measured by converters 110*a* and 110*b*, respectively, e.g., the initial output voltage of integrator 108*a* and 108*b* is measured between cycles. Measuring the initial output voltage of the integrator is more accurate than assuming the reset output voltage is "zero".

Figure 4:
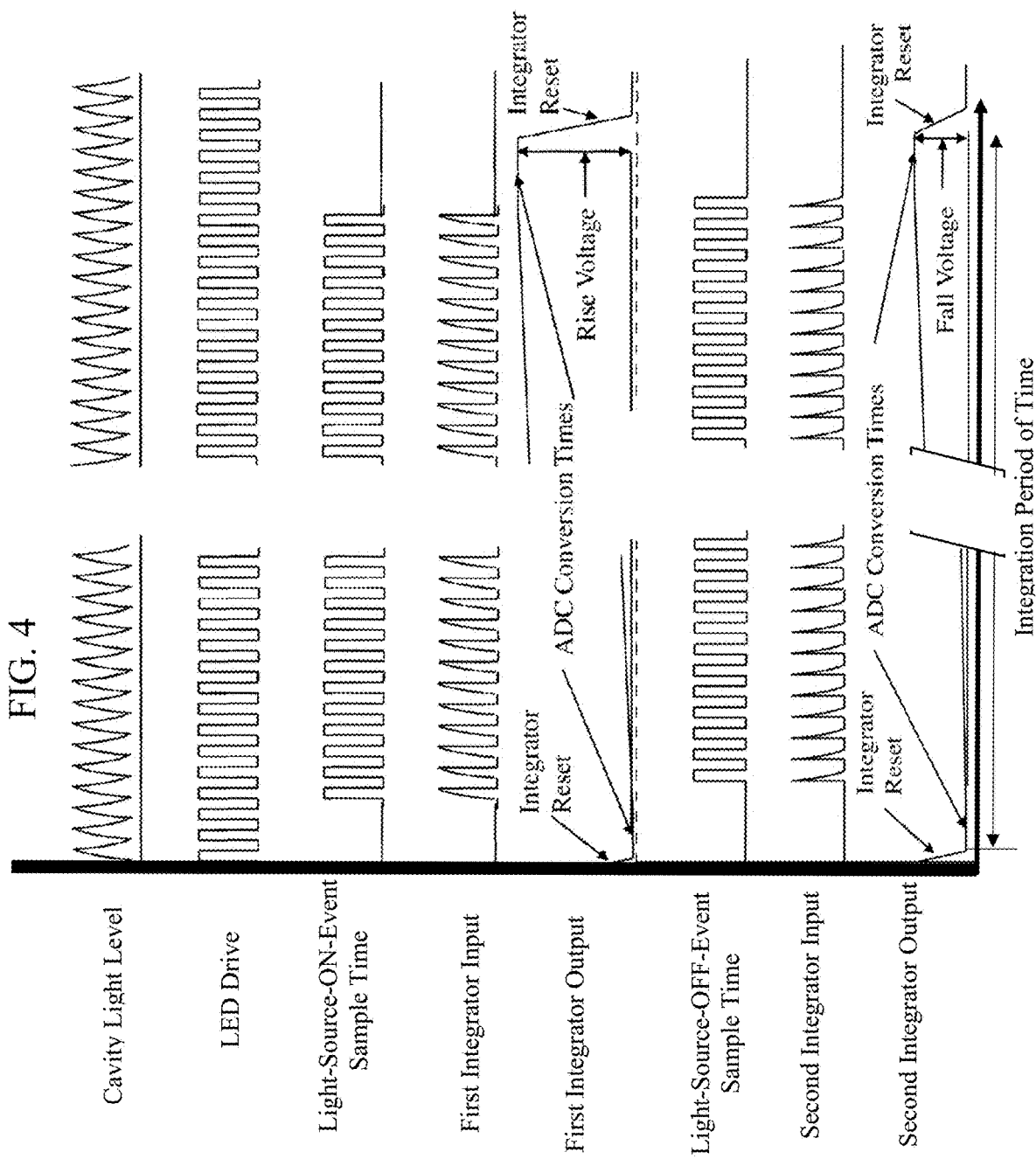
FIG. 4 is a graphical representation of an exemplary plurality of rise and fall measurements over an integration period of time according to one or more aspects of the disclosure.
Figure 5:
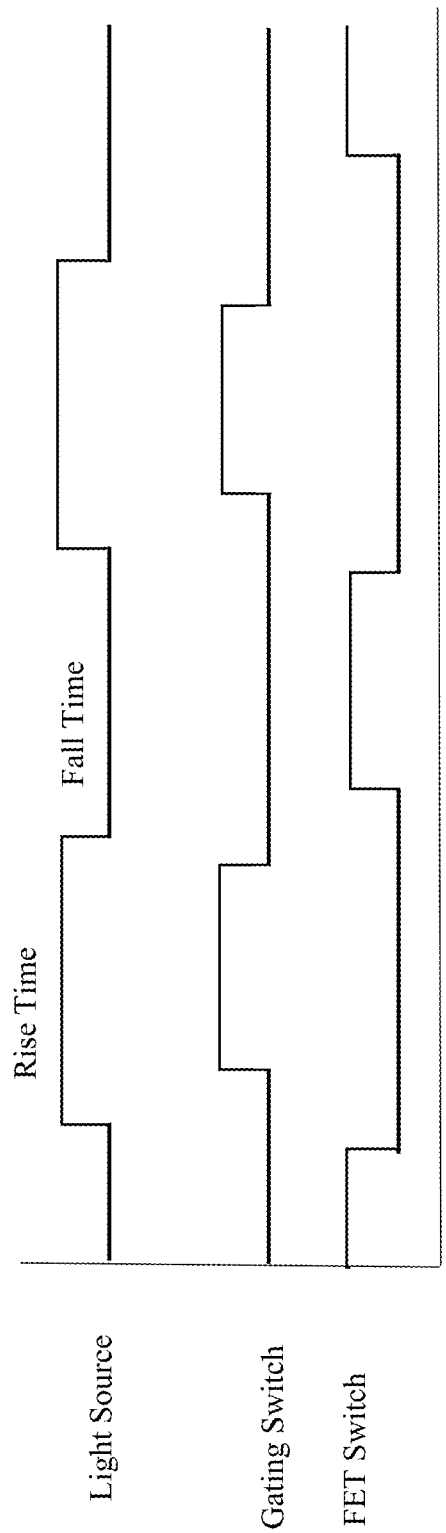
FIG. 5 is a graphical representation of a timing cycle according to one or more aspects of the disclosure.

FIG. 5 shows the timing diagram according to embodiments of the process. The difference between the final output voltage and the initial output voltage, e.g., the Rise Voltage of FIG. 4 shows the measure of charge (photons) collected during the sampling of the portions of the ON event "rise" time over the measurement interval (the integration period of time) and the simultaneously obtained portions of the OFF event "fall time" or "ring down" portion of the resonant cavity cycle. The "rise" time signal or ring-up (i.e., photons captured when LED 102 is ON) and the "fall" time signal or ring-down (i.e., photons captured when LED 102 is OFF) are consequently measured simultaneously and their totals for a measurement interval used to calculate a ratio, more particularly, the ratio of the difference between the rise time and the fall time (i.e., rise time minus fall time) divided by the sum of the rise time and the fall time (i.e., rise time plus fall time), represented by Equation 2 above:

$$\text{Ratio} = \frac{\text{rise time} - \text{fall time}}{\text{rise time} + \text{fall time}}. \qquad \text{Equation 2}$$

This ratio may be used to calculate the decay rate (k) represented by Equation 2. This ratio may also be the average of many measurements.

After measurement of the output voltage of the integrator 110, computer or processor 114 receives the given measurement (arrows 130*a* and 130*b*) and generates a reading. Such reading may be used to calculate the decay time constant ($\tau_0$) of an empty optical cavity 104 and changes in the decay time ($\tau$) caused by addition of an absorbing gas or scattering particles to the gas sample. The decay time constant ($\tau_0$) of an empty optical cavity 104 and changes in the decay time ($\tau$) are then used as a reference to calculate concentration of an absorbing gas (explained in more detail below). The concentration of the absorbing gas may be displayed on user interface 132 or sent to an external computer before or after processing using the external data link (arrow 134). Computer 114 also serves as the regulator and/or controller for the various functions while the CRDS 100 is in operation. For example, computer 114, which in some embodiments may be a single microchip, controls the square-wave drive of the light source 102 (arrow 102*a*), the sampling width, position and the interval of the measurement time (arrow 126) of detector 106, and resetting (arrow 128) of the integrator 108. Computer 114 may also serve to measure and control the environment (box 136), i.e., computer 114 can measure the atmospheric pressure and temperatures within the unit, and/or, stabilize the temperature of optical cavity 104 and electronics (i.e., making the quartz crystal oscillator 114*a* more stable) by controlling heaters to keep the temperature constant. Computer 114 may also serve to calculate the mathematical algorithms necessary to correlate the readings with the quantity of gas detected and/or measured.

FIG. 2 is a graphical representation of a "rise" time signal measurement generated from embodiments of the system during a predetermined time period. FIG. 2 illustrates the sample time signal in relation to the cavity light level, the LED drive and the gated integrator input (i.e., the gated photon generated current from the detector directed to a first integration circuit). More particularly, FIG. 2 illustrates the cavity light level as a function of the LED being turned ON and OFF. Referring to the LED Drive, the crest of the square wave represents when the LED is ON while the valley of the square wave represents when the LED is OFF. For the "rise" time signal measurement, a sample reading is taken during the time period when the LED is ON, i.e., the "ring up" or rise time.

FIG. 3 is a graphical representation of a "fall" time signal measurement generated from embodiments of the system during a predetermined time period. FIG. 3 illustrates the sample time signal in relation to the cavity light level, the LED drive and the integrator input (i.e., the gated photon generated current from the detector directed to the second integration circuit). More particularly, FIG. 3 illustrates the cavity light level as a function of the LED being turned ON and OFF. Referring to the LED Drive, the crest of the square wave represents when the LED is ON while the valley of the square wave represents when the LED is OFF. For the "fall" time signal measurement, a sample reading is taken during the time period when the LED is OFF, i.e., the "ring down" or fall time.

FIG. 4 is a graphical representation of an example rise time measurement interval. It depicts an ON-OFF time interval and an integration time period. It shows the resultant integrators output voltages for both the rise and the fall time. It also shows an example of the integrator reset time and the ADC conversion times just before the start of the next integration period of time and just after the completion of the previous integration period of time.

FIG. 5 is a graphical representation of the timing cycle. The top line shows the cycle of the light source. The Rise or Ring-up signal occurs when the light source is on, and the Fall or Ring-down signal occurs when the light source (e.g., a laser) is off.

The second line shows the action of the switching of the pairs of the gating circuitry, in this case FETs during the Rise signal. The initial charge created on the photodiode or phototube detector does not need to be immediately sampled, but a short delay will allow switching to not interfere with the previous measurement.

The third line shows the action of the switching of the pairs of FETs during the Fall signal. As in the rise, parasitic capacitance will allow the initial charge to be conveyed during the time that the FETs are active without interfering with the previous sampling. A measurement is still taken after over a volt of integration has occurred for each channel allowing for the determination of the voltage to microvolt resolution.

As shown in FIG. 4, there is also a period where the signal is reset. A voltage is acquired and amplified to reset the level for the next sampling period. This can occur at the end of the cycle so that the optimum portion signal at the beginning of each cycle is well measured.

As shown in FIGS. 6 and 7, which are a schematic representations showing the main components of the switching integration amplifier circuits (FIG. 6), and the end of cycle circuitry (FIG. 7) which resets the integration circuits prior to a subsequent integration period of time (after a first and before as second measurement time). In one or more embodiments, circuitry is utilized to ensure accuracy and precision in the zeroing of the integration circuits.

FIG. 6 shows the switching or gating circuitry for integration circuits according to embodiments of the disclosure. As shown in FIG. 6, each integration circuit receives input from a detector (e.g., a photodiode, a gated phototube, or the like). The input is switched by a matched pair of FETs so that each of the two integrating amplifiers collect a corresponding signal alternating between Rise processed by the first integrator and a fall processed by the second integrator. Prior to integration, it has been discovered that it is important to reset the voltage with each cycle so that just the current from the detector, representing one electron for each detected photon from the cavity, is integrated.

The integrating amplifiers have a capacitor for which the value depends on the magnitude of the signal being collected, for a smaller current, a smaller capacitance generates an equivalent voltage to a larger current with a larger capacitor.

At the test points Sig 1 and Sig 2, the voltage can be measured with a sensitive analog to digital converter, to get microvolt resolution on the signals. The vRef signal is applied both to the shield of the cable for the detector and to the signal line itself (not shown). The connection extending from the bottom of each integrating summing point provides a means for resetting the voltage at the end of a cycle when a series of collected Rise and Fall signals are sampled by the A/D converter. Typically, the period of each cycle may range from 1 microsecond to 100 microseconds, depending on the optimization of the characteristic baseline time constant of the pair of mirrors in the cavity. That time is chosen to be at an experimentally determined ideal level between the time of one and five time constants of the sample cell. The period of data collection is much longer and depends on the sampling frequency needed for testing. This sampling frequency may range from 10 Hz to 1 Hz but is typically chosen to match with the frequency of local alternating currents that are 60 Hz in the US and typically 50 Hz in Europe. With other regions adopting one or the other standard. Naturally there are frequencies such as 10 Hz that can match both frequencies in the same analyzer.

FIG. 7 shows the end of cycle sampling circuitry according to embodiments of the disclosure. As shown in FIG. 7, the input to the sampling circuit is tied to the summing point on each of two integrating amplifiers as shown in FIG. 6. The signals are amplified with an amplifier with high impedance inputs so that the impedance of the original summing point is maintained. The signal is then routed to the second channel to create a starting point for the next cycle.

The addition of an absorbing gas (such as certain gases found in the environment proximate to a target compound) causes the rise and fall times to decrease. These changes in the rise and fall times can be detected and measured and then used to calculate the amount of an absorbing gas present by comparison with the "no sample" reference data (explained previously). Thus, according to an embodiment of a method of the disclosure, the above process may be performed while a sample is introduced via sample inlet 118 and pumped out via pump outlet 120 to obtain data correlating to the introduced sample. In one embodiment, the sample may be introduced continuously. The SGID CRDS 100 may detect absorbing species in gas samples with any particles present filtered out or, alternatively, SGID CRDS 100 may detect particles if any absorbing gases such as $NO_2$ are removed, i.e., filtered out. Examples of absorbing gases that may be measured and quantified according to embodiments of the disclosure include, but are not limited to, nitrogen dioxide, nitrogen trioxide, fluorine, chlorine, bromine, iodine, ozone, sulfur dioxide, chlorine dioxide, $HO_2$ radicals, hydroxy radicals, and hydrocarbons, including aldehydes and aromatic species.

In contrast to prior art methods which look at decay rate only, the methods according to embodiments of the disclosure take into account both the rise and fall rates of the light emitted from a light source to generate a more precise reading of absorbing gases within a sample. Such method may be referred to as "time domain sampling." A key element to time domain sampling is the gated light detection performed by the detector, which allows photons to be detected and integrated without including wide bandwidth electronic noise associated with narrow time domain samples. Assuming photon noise dominates, the precision of a measurement may be doubled by increasing the integration time by a factor of four in view of that the photon noise level is the square root of the number of photons collected.

Representatively, a sample of 1000 collected photons results in a noise level of 3%, i.e., the square root of 1000 is approximately 30 which is then divided by 1000. On the other hand, a sample of 1,000,000 collected photons results in a noise level of 0.01%, i.e., the square root of 1,000,000 equals 1000 which is then divided by 1,000,000. Thus, according to an embodiment of the disclosure, integration of many samples gives a high photon count with a low noise, i.e., low signal to noise ratio, resulting in better precision and stability.

Advantageously, embodiments of devices and methods of the disclosure lend itself to higher precision stability via the more precise reference measurements (explained previously), temperature control, atmospheric pressure measurement, and a minimum number of analog and digital parts, e.g., low noise operational amplifier, a stable integrating capacitor, a high resolution delta-sigma ADC, the LED and the phototube. Moreover, embodiments of devices and methods of the disclosure lend itself to a minimum cost and minimum number of components for its performance capability. For example, buffers to drive the LED and the phototube, an integrator (an op amp, summing capacitor, and reset circuitry), a high resolution ADC, a display (an LCD driver and LCD) and an external interface can be controlled by a single chip microcontroller. Furthermore, embodiments of devices of the disclosure are flexible because many variables are controlled by the software, e.g., the cycle period, the LED ON and OFF time, the sample time, the reset time and the integration time. This lends itself to easy adjustability to, for example, changes in the optical cavity's length or mirror reflection coefficients can be accommodated by simply changing the measurement timing through changes in the software when needed. In some embodiments, the software can automatically optimize measurements.

In addition to the above, it has been discovered that by switching between two channels instead of collecting ring-up and ring-down signals as sets in series, there is a factor of 2 increase in the amount of light collected and the elimination of drift is achieved in Cavity Ring-Down Spectroscopy (CRDS). Gated Integration Detection integrates a series of ring-down signals and ring up signals to determine a ratio that can be converted to the time constant of the cavity. Any change in signal strength between the two sets results in an offset that can lead to drift.

Improvements of CRDS according to the instant disclosure allows the analyzer to achieve an increased signal that is still close to the photon limit. Where in general, it is accepted that CRDS will not achieve limits of detection closer than a factor of ten from the photon limit. This also allows for the use of a photodiode in place of a phototube with a factor of three increase in light sensitivity.

Furthermore, a set of field effect transistors is used to switch the signal of the ring-up and ring-down of the light in a CRDS cavity subjected to a laser or LED driven by a square wave with a period selected to optimize the amount of data collected.

The switched signal creates a current alternately into two integrating amplifiers with the resulting charge collected on a capacitor.

This concept is for a significant improvement on a previously patented method and system for cavity enhanced spectroscopy, in which ring-up and ring-down signals are obtained concurrently instead of in series, with the advantage of dramatically reduced warm-up and operational drift, and a factor of 2 increase in duty cycle, avoiding the loss of half of the total collectable signal.

While it has been established in prior art that in a CRDS system where there is a laser driven by a square wave that there is both a ring down when the light is turned off, and a ring up that can be separately integrated and normalized by dividing by the Sum to produce a Ratio with Ring-down over sum ranging from zero to one half, approaching one half asymptotically. This characteristic pair has an exponential up or down decay, characterized by a time constant or inversely a rate of decay that can be directly related to the path-length of the cavity in meters or kilometers or as a difference of the inverse as an absorbance in inverse distance units such as inverse centimeters.

The time constant is not directly derived from the ratio, because it is in multiple exponential factors and terms. It can be determined by reiterative calculation, by a look up table, or by plotting the equation for the ratio, reversing the axes to plot ratio versus Time constant, and fitting the resulting curve with a polynomial fit.

The method of gated integrated detection gates a photodetector on and off in sequence with the rise and fall signals integrating for many cycles sequentially, to integrate enough signal that a volt or more can be measured accurately approaching the photon limit.

In this new method, field effect transistors are used as a set to switch the current to one of two paths, integrating multiples of the alternate rise and fall signals concurrently. By collecting during the same time sequences, warm up and thermal drift can be cancelled with each set of measurements, resulting in a more precise measurement and reduced drift. Since there is no off time for the detector where a rise or fall is being discarded, there is also a near continuous measurement instead of a 50% duty cycle.

Furthermore, utilizing lasers which are OTS available at 405 nm may be used having outputs as high as a watt. In some embodiments, lasers having outputs in the range of 150-mW may be preferred due to higher operational temperatures on the order of 80° C. Mirrors can achieve path-lengths of 100-m to 2500-m in a 15-cm sample cell depending on their quality and how well they are tuned. Furthermore, it is have discovered that photodiode detectors can be as much as 3 times more sensitive than phototubes. Prior art CRDS instruments have demonstrated limits of detection near 10 ppt for detecting TNT in ambient atmosphere. Embodiments according to the instant disclosure have shown a 10 fold improvement over the prior art, suggesting that the instant SGID-CRDS method may obtain detection limits less than or equal to about 1 ppt under the same conditions.

EMBODIMENTS LISTING

Various aspects and embodiments of the instant disclosure include:

E1. A process comprising:
prov018ing a cavity ring down instrument comprising a light source in optical communication with a detector through an optical cavity;
the detector in electronic communication with a first integrating circuit and a second integrating circuit;
over an integrating period of time, repeatedly cycling the light source on in a light-source-on event to produce a plurality of individual ring up currents from the detector, each of the individual light-source-on events followed by a corresponding light-source-off event to produce a plurality of ring down currents from the detector;
for each of the light-source-on events and each of the light-source-off events, over the integration period of time, directing a portion of each ring up current to the first integrating circuit followed by directing a portion of each ring down current to the second integrating circuit to produce a total ring up current comprising a sum of the plurality of ring up currents obtained during the integration time and a total ring down current comprising a sum of the plurality of ring down currents obtained during that same integration time;
determining a rise time from the total ring up current; and
determining a fall time from the total ring down current.

2E. The process according to Embodiment 1E, wherein the first integrating circuit comprises:
a first dual N-channel and dual P-channel MOSFET pair configured to receive a first detection signal from the detector;
a first operational amplifier including a positive input configured to receive a first dual N-channel and dual P-channel MOSFET pair output signal and a negative input configured to receive a first operational output signal and
a second dual N-channel and dual P-channel MOSFET pair configured to receive the first operational output signal;
and wherein the second integrating circuit comprises:
a third dual N-channel and dual P-channel MOSFET pair configured to receive a second detection signal from the detector;
a second operational amplifier including a positive input configured to receive a third dual N-channel and dual P-channel MOSFET pair output signal and a negative input configured to receive a second operational output signal; and
a fourth dual N-channel and dual P-channel MOSFET pair configured to receive the second operational output signal.

3E. The process according to Embodiment 1E or 2E, wherein the detector is in gated electronic communication with the first integrating circuit and with the second integrating circuit through at least one field effect transistor.

4E. The process according to any one of Embodiments 1E through 3E, wherein the light source is light-emitting diode, a laser, or a combination thereof.

5E. The process according to any one of Embodiments 1E through 4E, wherein the light source is a multimode laser having a bandwidth of at least 10 nm optically coupled to a 10 nm band pass filter.

6E. The process according to any one of Embodiments 1E through 5E, wherein the optical cavity has an effective optical length of greater than or equal to about 10 meters.

7E. The process according to any one of Embodiments 1E through 6E, wherein a time for a single light-source-on event and/or a time for a single light-source-off event is less than or equal to about 500 microseconds.

8E. The process according to any one of Embodiments 1E through 7E, wherein a time for a single light-source-on event and/or a time for a single light-source-off event is less than or equal to about 1 microsecond.

9E. The process according to any one of Embodiments 1E through 8E, wherein the integrating period of time is greater than or equal to about 0.01 seconds.

10E. The process of claim 9, wherein the integrating period of time is less than or equal to about 1 second.

11E. The process according to any one of Embodiments 1E through 10E, wherein the detector includes a phototube, a photomultiplier, a photodiode, an avalanche photodiode, or a combination thereof.

12E. A system comprising:
a light source in optical communication with a detector through an optical cavity;
the detector in electronic communication through a gating circuit with a first integrating circuit and a second integrating circuit;
the light source, the detector, the gating circuit, and the integrating circuits in electronic communication with a processing system;
the processing system configured, over an integrating period of time, to repeatedly cycle the light source on in a light-source-on event to produce a plurality of individual ring up currents from the detector, each of the individual light-source-on events followed by a corresponding light-source-off event to produce a plurality of ring down currents from the detector;
for each of the light-source-on events, over the integration period of time, a portion of each ring up current is directed by the gating circuit to the first integrating circuit to produce a total ring up current including a sum of the plurality of ring up currents obtained during the integration time;
for each of the light-source-off events, over the integration period of time, a portion of each ring down current is directed by the gating circuit to the second integrating circuit to produce a total ring down current including a sum of the plurality of ring down currents obtained during that same integration time.

13E. The system according to Embodiment 12E, wherein the first integrating circuit comprises:
a first dual N-channel and dual P-channel MOSFET pair configured to receive a first detection signal from the detector;
a first operational amplifier including a positive input configured to receive a first dual N-channel and dual P-channel MOSFET pair output signal and a negative input configured to receive a first operational output signal and a second dual N-channel and dual P-channel MOSFET pair configured to receive the first operational output signal;
and wherein the second integrating circuit comprises:
a third dual N-channel and dual P-channel MOSFET pair configured to receive a second detection signal from the detector;
a second operational amplifier including a positive input configured to receive a third dual N-channel and dual P-channel MOSFET pair output signal and a negative input configured to receive a second operational output signal; and
a fourth dual N-channel and dual P-channel MOSFET pair configured to receive the second operational output signal.

14E. The system according to Embodiment 12E or 13E, wherein the detector is in gated electronic communication with the first integrating circuit and with the second integrating circuit through at least one field effect transistor.

15E. The system according to anyone of Embodiments 12E through 14E, wherein the light source is light-emitting diode, a laser, or a combination thereof.

16E. The system according to anyone of Embodiments 12E through 15E, wherein the light source is a multimode laser having a bandwidth of at least 10 nm optically coupled to a 10 nm band pass filter.

17E. The system according to anyone of Embodiments 12E through 16E, wherein the optical cavity has an effective optical length of greater than or equal to about 10 meters.

18E. The system according to anyone of Embodiments 12E through 17E, wherein a time for a single light-source-on event and/or a time for a single light-source-off event is less than or equal to about 500 microseconds.

19E. The system according to anyone of Embodiments 12E through 18E, wherein a time for a single light-source-on event and/or a time for a single light-source-off event is less than or equal to about 1 microsecond.

20E. The system according to anyone of Embodiments 12E through 19E, wherein the integrating period of time is greater than or equal to about 0.01 seconds.

While certain exemplary embodiments have been described and shown in the accompanying drawings, it is to be understood that such embodiments are merely illustrative of and not restrictive on the broad disclosure, and that this disclosure is not be limited to the specific constructions and arrangements shown and described, since various other modifications may occur to those ordinarily skilled in the art.

previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of:" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A process comprising:
   providing a cavity ring down instrument comprising a light source in optical communication with a detector through an optical cavity;
   the detector in electronic communication with a first integrating circuit and a second integrating circuit;
   over an integrating period of time, repeatedly cycling the light source on in a light-source-on event to produce a plurality of individual ring up currents from the detector, each of the individual light-source-on events followed by a corresponding light-source-off event to produce a plurality of ring down currents from the detector;
   for each of the light-source-on events and each of the light-source-off events, over the integration period of time, directing a portion of each ring up current to the first integrating circuit followed by directing a portion of each ring down current to the second integrating circuit to produce a total ring up current comprising a sum of the plurality of ring up currents obtained during the integration time and a total ring down current comprising a sum of the plurality of ring down currents obtained during that same integration time;
   determining a rise time from the total ring up current; and
   determining a fall time from the total ring down current.

2. The process of claim 1, wherein the first integrating circuit comprises:
   a first dual N-channel and dual P-channel MOSFET pair configured to receive a first detection signal from the detector;
   a first operational amplifier including a positive input configured to receive a first dual N-channel and dual P-channel MOSFET pair output signal and a negative input configured to receive a first operational output signal and
   a second dual N-channel and dual P-channel MOSFET pair configured to receive the first operational output signal;
   and wherein the second integrating circuit comprises:
   a third dual N-channel and dual P-channel MOSFET pair configured to receive a second detection signal from the detector;
   a second operational amplifier including a positive input configured to receive a third dual N-channel and dual P-channel MOSFET pair output signal and a negative input configured to receive a second operational output signal; and
   a fourth dual N-channel and dual P-channel MOSFET pair configured to receive the second operational output signal.

3. The process of claim 1, wherein the detector is in gated electronic communication with the first integrating circuit and with the second integrating circuit through at least one field effect transistor.

4. The process of claim 1, wherein the light source is light-emitting diode, a laser, or a combination thereof.

5. The process of claim 1, wherein the light source is a multimode laser having a bandwidth of at least 10 nm optically coupled to a 10 nm band pass filter.

6. The process of claim 1, wherein the optical cavity has an effective optical length of greater than or equal to about 10 meters.

7. The process of claim 1, wherein a time for a single light-source-on event and/or a time for a single light-source-off event is less than or equal to about 500 microseconds.

8. The process of claim 1, wherein a time for a single light-source-on event and/or a time for a single light-source-off event is less than or equal to about 1 microsecond.

9. The process of claim 1, wherein the integrating period of time is greater than or equal to about 0.01 seconds.

10. The process of claim 9, wherein the integrating period of time is less than or equal to about 1 second.

11. The process of claim 1, wherein the detector includes a phototube, a photomultiplier, a photodiode, an avalanche photodiode, or a combination thereof.

12. A system comprising:
    a light source in optical communication with a detector through an optical cavity;
    the detector in electronic communication through a gating circuit with a first integrating circuit and a second integrating circuit;
    the light source, the detector, the gating circuit, and the integrating circuits in electronic communication with a processing system;
    the processing system configured, over an integrating period of time, to repeatedly cycle the light source on in a light-source-on event to produce a plurality of individual ring up currents from the detector, each of the individual light-source-on events followed by a corresponding light-source-off event to produce a plurality of ring down currents from the detector;
    for each of the light-source-on events, over the integration period of time, a portion of each ring up current is directed by the gating circuit to the first integrating circuit to produce a total ring up current including a sum of the plurality of ring up currents obtained during the integration time;
    for each of the light-source-off events, over the integration period of time, a portion of each ring down current is directed by the gating circuit to the second integrating circuit to produce a total ring down current including a sum of the plurality of ring down currents obtained during that same integration time.

13. The system of claim 12, wherein the first integrating circuit comprises:
    a first dual N-channel and dual P-channel MOSFET pair configured to receive a first detection signal from the detector;
    a first operational amplifier including a positive input configured to receive a first dual N-channel and dual P-channel MOSFET pair output signal and a negative input configured to receive a first operational output signal and
    a second dual N-channel and dual P-channel MOSFET pair configured to receive the first operational output signal;
    and wherein the second integrating circuit comprises:
    a third dual N-channel and dual P-channel MOSFET pair configured to receive a second detection signal from the detector;
    a second operational amplifier including a positive input configured to receive a third dual N-channel and dual P-channel MOSFET pair output signal and a negative input configured to receive a second operational output signal; and a fourth dual N-channel and dual P-channel MOSFET pair configured to receive the second operational output signal.

14. The system of claim 12, wherein the detector is in gated electronic communication with the first integrating circuit and with the second integrating circuit through at least one field effect transistor.

15. The system of claim 12, wherein the light source is light-emitting diode, a laser, or a combination thereof.

16. The system of claim 12, wherein the light source is a multimode laser having a bandwidth of at least 10 nm optically coupled to a 10 nm band pass filter.

17. The system of claim 12, wherein the optical cavity has an effective optical length of greater than or equal to about 10 meters.

18. The system of claim 12, wherein a time for a single light-source-on event and/or a time for a single light-source-off event is less than or equal to about 500 microseconds.

19. The system of claim 12, wherein a time for a single light-source-on event and/or a time for a single light-source-off event is less than or equal to about 1 microsecond.

20. The system of claim 12, wherein the integrating period of time is greater than or equal to about 0.01 seconds.

* * * * *